United States Patent [19]

Tamura et al.

[11] Patent Number: 5,250,713
[45] Date of Patent: Oct. 5, 1993

[54] PROCESS FOR PRODUCING DESULFURIZED FATS AND OILS OR FATTY ACID ESTERS AND PROCESS FOR PRODUCING ALCOHOLS BY USING SAID DESULFURIZED FATS AND OILS OR FATTY ACID ESTERS

[75] Inventors: Hiroyuki Tamura; Yasuyuki Hattori; Kunizo Hashiba; Osamu Tabata; Kiyoshi Tsukada; Noriaki Fukuoka, all of Wakayama, Japan

[73] Assignee: Kao Corporation, Tokyo, Japan

[21] Appl. No.: 849,187

[22] Filed: Mar. 11, 1992

[30] Foreign Application Priority Data

Mar. 11, 1991 [JP] Japan .................. 3-44708
Nov. 19, 1991 [JP] Japan ................. 3-303202

[51] Int. Cl.$^5$ ............................................. C07C 51/36
[52] U.S. Cl. .................................... 554/141; 554/175; 554/85; 554/194; 568/831; 568/864; 568/885
[58] Field of Search ............... 554/141, 93, 175, 85; 568/831, 864, 885, 176

[56] References Cited

U.S. PATENT DOCUMENTS 5,120,885  6/1992  Tsukada et al. .................... 568/885

Primary Examiner—Paul F. Shaver
Assistant Examiner—Deborah D. Carr
Attorney, Agent, or Firm—Sughrue, Mion, Zinn, Macpeak & Seas

[57] ABSTRACT

A process for producing desulfurized fats and oils or fatty acid esters is disclosed, which comprises treating fats and oils or fatty acid esters under hydrogen or a mixture of hydrogen and an inert gas atmosphere at a pressure of from 0.1 to 500 kg/cm$^2$ in the absolute pressure at a temperature of from 100° to 350° C. in the presence of a catalyst of the following formula (I):

$$Cu \cdot X_x \cdot Y_y \cdot O_z \qquad (I)$$

wherein all symbols are defined in the disclosure. A process for producing an alcohols using desulfurized fats and oils or fatty acid esters is also disclosed. According to the process for producing an alcohol of the present invention, an alcohol of a high purity and good qualities can efficiently and effectively be produced.

9 Claims, No Drawings

PROCESS FOR PRODUCING DESULFURIZED FATS AND OILS OR FATTY ACID ESTERS AND PROCESS FOR PRODUCING ALCOHOLS BY USING SAID DESULFURIZED FATS AND OILS OR FATTY ACID ESTERS

FIELD OF THE INVENTION

This invention relates to a process for producing desulfurized fats and oils or fatty acid esters and a process for producing alcohols by using the desulfurized fats and oils or fatty acid esters.

More particularly, it relates to a process for producing desulfurized fats and oils and fatty acid esters by catalytically hydrogenating various fats and oils or fatty acid esters to thereby give the corresponding hydrogenated fatty acids, aliphatic alcohols or aliphatic amines, wherein the starting material is preliminarily treated with a specific catalyst containing copper to thereby reduce a content of sulfur which acts as a catalyst poison. The present invention further relates to a process for producing alcohols by catalytically reducing fats and oils or fatty acid esters with hydrogen in the presence of a catalyst for ester reduction, wherein the aforesaid desulfurized fats and oils or fatty acid esters are used to thereby extend the catalyst life of said catalyst for ester reduction.

BACKGROUND OF THE INVENTION

Fats and oils (the expression "fats and oils" as used herein means triglycerides) and fatty acid esters (the expression "fatty acid esters" as used herein means esters, except triglycerides, of fatty acids and lower or higher alcohols) generally contain at least several to several tens of ppm of sulfur. These raw materials will hereinafter sometimes be referred to as "starting materials" or "starting oils". When hydrogenated fatty acids, aliphatic alcohols or aliphatic amines are to be produced from these starting oils, a trace amount of sulfur compounds contained therein would deteriorate a hydrogenation catalyst employed in each production step and thus cause a marked reduction of its catalytic life. In particular, when these starting oils are catalytically reduced with hydrogen in the presence of a catalyst for ester reduction, a trace amount of sulfur compounds contained therein would act as a catalyst poison and thus seriously reduce the duration of the catalyst for ester reduction.

Under these circumstances, the present inventors have conducted studies of purification methods for the aforesaid starting oils to reduce the sulfur content thereof and, as a result, brought out the following problems.

(1) Problem of Purification by Distillation

When methyl esters of fatty acids which are derived from natural fats and oils in a conventional manner are subjected to distillation in a yield of 90% or 98%, the sulfur content can be reduced to 10% or 20%, respectively, of the initial content. However, where fatty acid methyl esters which are usually available or prepared are distilled for meeting the purpose of sulfur content reduction, there is an unavoidable distillation loss of at least 5%, and the alkyl distribution of the starting material varies largely.

In the case of fats and oils or fatty acid esters of higher alcohols, because of the high boiling point thereof, it is difficult to remove the sulfur compounds from such starting materials by distillation.

(2) Problems of Purification with Catalyst for Desulfurization

In the field of petroleum refining, molybdenum or tungsten catalysts are used for removing sulfur compounds from light oil and heavy oil as disclosed, for example, in Shokubai Process Kacaku (Catalytical Process Chemistry), published by Tokyo Kagaku Dojin Shuppan, pages 377–408 (1984).

The catalysts require temperatures of 300° C. or higher for manifestation of the desulfurization activity. If fats and oils or fatty acid esters are hydrogenated in such high temperatures, hydrogenolysis of the ester group occurs, which brings about an increase in the acid value (AV) and a marked increase of decomposition products of the starting material. In addition, a catalyst component is dissolved by the produced fatty acids which adversely affects selectivity of the catalyst in the ester reduction reaction.

SUMMARY OF THE INVENTION

Accordingly, it is an object of the present invention to provide a process for producing desulfurized fats and oils and fatty acid esters containing a reduced content of sulfur which acts as a catalyst poison, as well as a process for efficiently producing alcohols of good qualities and a high purity at a high yield by catalytically reducing fats and oils or fatty acid esters in the presence of a catalyst for ester reduction without shortening the catalyst life of the catalyst for ester reduction.

The present inventors have conducted extensive studies in order to establish a purification technique in the production of alcohols from fats and oils or fatty acid esters whereby the sulfur content of starting oils can be reduced to a desired level. As a result, they have found out that starting oils suitable for the purpose can be efficiently produced by treating fats and oils or fatty acid esters with a specific catalyst under a hydrogen and/or an inert gas atmosphere, thus completing the present invention.

Accordingly, the present invention provides a process for producing alcohols by catalytically reducing fats and oils or fatty acid esters with hydrogen in the presence of a catalyst for ester reduction, wherein the fats and oils or fatty acid esters are previously treated under a hydrogen or a mixture of hydrogen and an inert gas atmosphere in the presence of a catalyst represented by the following formula (I) at a temperature of from 100° to 350° C. to yield a sulfur content of the fats and oils or fatty acid esters of 0.6 ppm or lower:

$$Cu \cdot X_x \cdot Y_y \cdot O_z \qquad (I)$$

wherein X represents an element selected from Fe, Zn and Cr;

Y represents an element selected from Al, Si and Ti;

x and y each represents an atomic ratio determined by referring Cu as 1, provided that x is a value from 0.02 to 2.4 and y is a value from 0 to 2.0; and z is an atomic ratio of oxygen satisfying the valence requirements of the elements represented by X and Y.

The present invention further provides a process for producing desulfurized fats and oils or fatty acid esters which comprises treating fats and oils or fatty acid esters under hydrogen and/or an inert gas atmosphere at a pressure of from 0.1 to 20 kg/cm² in the absolute pressure at a temperature of from 100° to 350° C. in the presence of the catalyst of formula (I).

DETAILED DESCRIPTION OF THE INVENTION

Now the present invention will be described in detail.

In the production of aliphatic alcohols by catalytically reducing fats and oils or fatty acid esters with hydrogen in the presence of a catalyst for ester reduction, the catalyst life is influenced greatly by the qualities of these starting oils. The present inventors have examined closely impurities in the starting oils which have great influences on the duration of the catalyst for ester reduction and found out that, in addition to sulfur compounds and halogen compounds conventionally known as catalyst poisons, free fatty acids also act as an extremely strong catalyst poison. Sulfur compounds and halogen compounds are known generally as poisons for catalyst for hydrogenation, and it is therefore desirable to reduce these poisonous substances as much as possible when hydrogenation reactions are conducted. Since the halogen content of usual starting oil is very low, it is the most important to reduce the sulfur content. Further, industrially employed catalysts for ester reduction are copper-chromium catalyst and copper-zinc ones which are susceptible to corrosion by free fatty acids. Therefore, it is also important to minimize the content of free fatty acids in the starting oils.

To determine permissible content of sulfur compounds and free fatty acids in the starting oils, the inventors carried out experiments by using methyl esters derived from coconut oil or palm kernel oil in a usual manner with a copper-based catalyst. For comparison, methyl esters obtained by distillation of the same starting oil (distillation yield: 90%) which have a sulfur content of from 0.3 to 0.4 ppm and an acid value (AV) of 0.1 mgKOH/g or less were used. It was confirmed that substantially the same catalyst durability as obtained when using distilled methyl esters can be assured by using a starting material having a sulfur content of not more than 0.6 ppm, more preferably not more than 0.3 ppm, and an acid value (AV) of not more than 2.

Sulfur compounds present in the starting oils cannot be removed completely by common purification procedures such as treatment with an adsorbent, alkali treatment and steaming. Those purification procedures, even when sufficiently performed, still leave about 3 to 5 ppm of a sulfur content. Attempts to reduce further the sulfur content by such customary purification operations were unsuccessful. Thus, under the present situation, there has been no means but to conduct purification by distillation. On the other hand, free fatty acids can be reduced easily by common purification procedures, such as alkali treatment and steaming.

Accordingly, the present invention provides a economical and efficient purification process, as a substitute for the conventional distillation purification, for reducing the sulfur content of the fats and oils and the fatty acid esters as well as a process for producing alcohols with the use of starting materials of a low sulfur content obtained by the aforesaid purification treatment.

As a matter of course, the fats and oils or fatty acid esters may be subjected to a distillation treatment prior to be subjected to the purification process of the present invention in which the fats and oils or fatty acid esters are treated under a specific condition in the presence of the catalyst of formula (I).

Examples of the fats and oils to be used in the present invention include vegetable and animal fats and oils such as coconut oil, palm oil, palm kernel oil, soybean oil, rape seed oil, beef tallow, lard and fish oil and those obtained by hydrogenating these fats and oils.

The fatty acid esters to be used in the present invention include those derived from the above-mentioned fats and oils and esters of a lower or higher alcohol with a fatty acid having 1 to 24 carbon atoms. Examples of the fatty acids constituting these fatty acid esters include caproic acid, caprylic acid, capric acid, lauric acid, myristic acid, palmitic acid, stearic acid, eicosanoic acid, docosanoic acid, oleic acid and erucic acid. Examples of the alcohols constituting the fatty acid esters include straight-chain or branched and saturated or unsaturated alcohols having 1 to 24 carbon atoms. Specific examples thereof include methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerol and trimethylolpropane.

Desulfurization process

The copper-containing catalyst to be used in the present invention for desulfurization and purification has a composition represented by the above formula (I). From the viewpoint of desulfurization activity, the composition of the desulfurization catalyst of formula (I) is highly important.

Preferred examples of the desulfurization catalyst of formula (I) include those having the element composition of Cu—Fe—O, Cu—Fe—Al—O, Cu—Fe—Al—Zn—O, Cu—Ti—O, Cu—Zn—O, Cu—Zn—Ti—O, Cu—Si—O, Cu—Zn—Si—O, Cu—Cr—O and Cu—Cr—Zn—O.

The method for producing the desulfurization catalyst of formula (I) is not particularly restricted. Thus it may be obtained by preparing a mixture comprising compounds containing the elements specified in formula (I) using either a coprecipitation method, impregnation method or uniform kneading method or a combination of these method and calcining the resulting mixture. Among the method for preparing the mixture comprising compounds containing the elements, the coprecipitation method is generally employed. Details of the methods for producing the desulfurization catalyst are described, for example, in *Syokubai Chosei Kagaku* (Catalyst Preparation Chemistry), published by Kodansha Scientific, pages 13–56 (1980).

The catalyst of formula (I) to be used in the present invention may be supported or mixed with a carrier. The carrier to be used in the present invention and a method for supporting or mixing the desulfurization catalyst with the carrier are described, for example, in *Syokubai Chosei-Ho* (Method for Preparation of Catalyst), published by Kodansha Scientific, pages 16–63 (1974). Specific examples of the carrier include silica, alumina, silica-alumina, zeolite, diatomaceous earth, acid clay, titania, zirconia and activated carbon. The catalyst of formula (I) containing the carrier may be used, depending on the treatment method, in the form of powders or a molded form such as a spherical or column form. The catalyst is activated by reduction with hydrogen on use. In some cases, the catalyst may previously be activated by reduction and stabilized in a known manner and used as such or after re-activated by reduction.

The aforesaid desulfurization treatment may be effected continuously, semi-batchwise or batchwise. For mass treatment, a continuous reaction system is preferred. Continuous treatment can be carried out in any of many widely practiced reaction systems such as a fixed bed system, a moving bed system, a fluidized bed system or systems used, for example, in petroleum refining, e.g., catalytic desulfurization, catalytic cracking and catalytic reforming. In general, where the starting oils have a relatively low sulfur content, a fixed bed system in which a catalyst can be used in a high concentration is preferred. Where the starting oils have a high sulfur content, the treatment may be performed in a moving bed or fluidized bed system in which a spent catalyst having reduced activity can be exchanged continuously.

Details of the fixed bed system which can be used in the present invention are described, for example, in *The Oil and Gas Journal*, May 25, 1966, pages 173–178 (1066) and *Hydrocarbon Processing*, November, 1970, pages 187–191 (1970). Details of the fluidized bed system which can be used in the present invention are described, for example, in G. Diecklmann and H. J. Heinz, *The Basics of Industrial Oleochemistry*, published by Peter Promp GmbH., pages 91–102 (1988). Details of the moving bed system which can be used in the present invention are described, for example, in W. C. van Zijll Langhout et al., *The Oil and Gas Journal*, December, pages 120–126 (1980).

According to the present invention, the starting fats and oils or fatty acid esters are treated in the presence of the above-mentioned catalyst of formula (I) in, for example, a fixed bed continuous reaction system under the following conditions.

The flowing gas is hydrogen or a mixture of hydrogen and an inert gas examples of which include nitrogen, argon, helium and methane. The treating pressure ranges from 0.1 to 500 kg/cm$^2$ (in the absolute pressure; the same will apply to hereinafter).

In the fixed bed continuous reaction system, the starting oil to be treated may be passed either as an upward parallel flow (up-flow system), a downward parallel flow (trickle flow system) or as a counter flow (counter flow system). However the counter flow system is disadvantageous where a large amount of a liquid or a gas is to be passed. On the other hand, the up-flow system is disadvantageous from the viewpoint of the necessity of the catalyst strength and pressure loss of the gas flow. In these cases, therefore, it is preferred to employ the trickle flow system.

Next, a low pressure treatment (treating pressure: from 0.1 to 20 kg/cm$^2$) and a high pressure treatment (treating pressure: from more than 20 kg/cm$^2$ to 500 kg/cm$^2$) will be illustrated.

(i) Low pressure treatment

In this case, the treating pressure preferably ranges from 1 to 5 kg/cm$^2$, from the viewpoint of the desulfurization activity and the suppression of the starting oils from decomposition. When the treating pressure is elevated under a hydrogen gas atmosphere, the amount of by-products due to hydrogenation decomposition of the starting oils increases as the desulfurization proceeds. The treating temperature may be determined within a range of from 100° to 350° C. At lower temperatures, the desulfurization activity is lowered. At higher temperatures, the amount of by-products due to thermal decomposition of the starting oils increases. Thus it is preferred to carry out the treatment within a temperature range of from 150° to 300° C.

Flow velocity of the starting oil is preferably controlled as to give a volume ratio to the reaction tower per hour (i.e., liquid hourly space velocity, hereinafter abbreviated as LHSV) of from 0.1 to 5.0 Hr$^{-1}$, though the productivity is lowered with a decrease in the LHSV.

When the sulfur compounds contained in fats and oils and fatty acid esters are purified and eliminated under the above-mentioned conditions, some conditions may have to be selected to maintain the sulfur content to 0.6 ppm or below but may increase an acid value (AV). Where the purification treatment is conducted under such conditions which may cause an increase in an acid value (AV), it is permitted to previously add a mono- or polyhydric alcohol having from 1 to 18 carbon atoms to the starting oil whereby free fatty acids produced during the purification treatment are esterified with the added alcohol to thereby reduce the acid value (AV) to an acceptable level. The alcohol is added in an amount of from 10 to 1000 moles, and preferably from 20 to 500 moles, per mol of free fatty acids produced or estimated to be produced under such conditions. Examples of usable mono- or polyhydric alcohols having from 1 to 18 carbon atoms include methanol, ethanol, propanol, isopropanol, butanol, secbutanol, t-butanol, pentanol, hexanol, heptanol, octanol, decanol, dodecanol, tetradecanol, hexadecanol, octadecanol, ethylene glycol, propylere glycol, butanediol and glycerol.

The desulfurized fats and oils or fatty acid esters thus obtained are usable not only as starting materials for producing alcohols but also as starting materials for producing hydrogenated fatty acids or aliphatic amines.

(ii) High pressure treatment

In this case, fats and oils or fatty acid esters are treated in the presence of a desulfurization catalyst represented by formula (I) under conditions as specified below.

In the case of a continuous reaction system, for example, the treating flowing gas is hydrogen or a mixture of hydrogen and an inert gas mixture. Examples of the inert gas include nitrogen, argon, helium and methane. The flow rate of hydrogen or a hydrogen-containing mixed gas is determined arbitrarily within such a range that the molar ratio of hydrogen to the ester group content of the starting oils which is calculated from the saponification value (SV) is from 0.1 to 300. The pressure of feeding gas may be controlled so as to a partial pressure of hydrogen ranges from more than 20 kg/cm$^2$ to 500 kg/cm$^2$, preferably from 30 kg/cm$^2$ to 300 kg/cm$^2$. When the molar ratio of hydrogen to the ester group and pressure are lowered, the desulfurization activity decreases. The treating temperature may be determined within a range of from 100° to 350° C. At a lower temperature, the desulfurization activity decreases. At a higher temperature, on the other hand, the amount of by-products due to the decomposition of the starting oils increases. Therefore this treatment may be preferably carried out within a temperature range of from 150° to 300° C.

Flow velocity of the fats and oils or fatty acid esters to be treated (i.e., the starting oil) is controlled as to give a volume ratio to the reaction tower per hour (liquid hourly space velocity, hereinafter abbreviated as LHSV) of from 0.1 to 5.0 Hr$^{-1}$. A decrease in the LHSV is disadvantageous from the viewpoint of productivity. When a liquid phase suspended bed system is employed, the catalyst concentration is arbitrarily determined within a range of from 0.05 to 20% by weight.

In the treatment of the fats and oils or fatty acid esters under the aforesaid conditions, the sulfur content should be minimized as low as possible. As the results of study, the present inventors have found out that the influences of sulfur content on the duration of the life of a copper-based catalyst for ester reduction can be relieved to an almost ignorable level by reducing the sulfur content to 0.6 ppm or less.

It is therefore desirable that the sulfur content of the fats and oils or fatty acid esters obtained by the purification process of the present invention has been reduced to 0.6 ppm or less. In order to stably produce fats and oils or fatty acid esters of a sulfur content of 0.6 ppm or less for a long time, it is important to maintain the saponification value (SV) of the oil obtained in the aforesaid conditions at 180 mgKOH/g or less.

Namely, when the reaction condition is controlled so as to give fats and oils or fatty acid esters of a low saponification value (SV), although a high desulfurization rate can be maintained for a short period of time, it is difficult to maintain the sulfur content of the treated oil at 0.6 ppm or less for a prolonged period of time. On the other hand, when the reaction condition is controlled so as to give fats and oils or fatty acid esters of an excessively high saponification value (SV), desulfurization cannot sufficiently performed.

Accordingly, when the aforesaid treatment is conducted in a continuous reaction system, it is desirable to control the conditions in such a manner as to maintain the saponification value (SV) of the treated oil at 180 mgKOH/g or less, and preferably from 50 to 150 mgKOH/g.

Process for Producing Alcohol by Catalytic Reduction

The fats and oils or fatty acid esters of a sulfur content of 0.6 ppm or below, which have been obtained by the purification process of the present invention, can be then converted into the corresponding alcohols by catalytically reducing with hydrogen in the presence of a catalyst for ester reduction. As the catalyst for ester reduction to be used here, copper-based catalysts for ester reduction are preferable. For example, known catalyst systems such as copper-chromium, copper-zinc, copper-iron-aluminum and copper-silica may be cited. The ester reduction may be effected in the presence of the aforesaid catalyst either in a liquid phase suspended bed system or in a fixed bed system.

Conditions for the ester reduction may be selected in accordance with those commonly known in the art. When a liquid phase suspended bed system is employed, the catalyst is preferably used in an amount of from 0.1 to 20% by weight based on the starting fats and oils or fatty acid esters, though the catalyst amount may be optionally selected depending on the reaction temperature or the reaction pressure within a range yielding a reaction rate sufficient for practical production. The reaction temperature may range from 160° to 350° C., preferably from 200° to 280° C. The reaction pressure may range from 1 to 350 kg/cm², preferably from 30 to 300 kg/cm².

When a fixed bed system is employed, the catalyst is employed in a molded from such as column, pellet or spherical form. The reaction temperature may range from 130° to 300° C., preferably from 160 to 270° C. The reaction pressure may range from 0.1 to 300 kg/cm². The LHSV preferably ranges from 0.5 to 5 Hr$^{-1}$ in terms of production or reaction efficiency, though it may be optionally selected depending on the reaction conditions.

The present invention is now illustrated in greater detail with reference to Examples, but it should be understood that the present invention is not deemed to be limited thereto.

PREPARATION EXAMPLE I

Desulfurization Catalyst A 273 g of pure water was introduced into a 2 l four-neck flask provided with a stirrer and a thermometer and heated to 90° C. Then an aqueous solution of metal salts, prepared by dissolving 66.4 g of $Cu(NO_2)_2.3H_2O$ and 53.3 g of $Zn(NO_3)_2.6H_2O$ in 190 g of pure water, and a 17% by weight aqueous solution of sodium carbonate were simultaneously added dropwise thereto, while maintaining the pH value of the reaction mixture at 5.7 to 6.3. Next, a 10% by weight aqueous solution of sodium hydroxide was added thereto to thereby adjust the pH value to 9.5. The precipitate thus formed was filtered, washed with water, dried and then calcined at 450° C. for 2 hours. Thus an oxide having a composition of an atomic ratio of Cu:Zn:O=1:0.65:1.65 was obtained. This oxide is hereinafter referred to as Desulfurization Catalyst A.

PREPARATION EXAMPLE II

Desulfurization Catalyst B 300 g of pure water and 17.2 g of titanium oxide were introduced into a 2 l four-neck flask provided with a stirrer and a thermometer and heated to 98° C. Then a mixed aqueous solution of 65.0 g of $Cu(NO_3)_2. 3H_2O$ and 4.0 g of $Zn(NO_3)_2.6H_2O$ and a 10% by weight aqueous solution of sodium carbonate were simultaneously added dropwise thereto, while maintaining the pH value of the reaction mixture at 5 to 6. Next, a 10% by weight aqueous solution of sodium hydroxide was added until the pH value of the mixture reached 9. The precipitate thus formed was filtered, washed with water, dried and then calcined at 450° C. for 2 hours. Thus an oxide having a composition of an atomic ratio of Cu:Zn:Ti:O=1:0.05:0.8:2.65 was obtained. This oxide is hereafter referred to as Desulfurization Catalyst B.

PREPARATION EXAMPLE III

Desulfurization Catalyst C 762 g of pure water, 44.6 g of sodium aluminate, 113.2 g of $CuSO_4.5H_2O$ and 151.2 g of $FeSO_4.7H_2O$ were introduced into a 2 l four-neck flask provided with a stirrer and a thermometer and heated to 98° C. Then 528.3 g of a 22% by weight aqueous solution of sodium carbonate was added dropwise thereto within 120 minutes. Next, a 10% by weight aqueous solution of sodium hydroxide was added until the pH value of the mixture reached 10.5. The precipitate thus formed was filtered, washed with water, dried and then calcined at 600° C. for 1 hour. Thus an oxide having a composition of an atomic ratio of Cu:Fe:Al:O=1:1.1:1.2:4.2–4.5 was obtained. This oxide is hereinafter referred to as Desulfurization Catalyst C.

PREPARATION EXAMPLE IV

Desulfurization Catalysts D and E

Catalysts comprising oxides of compositions respectively having the following atomic ratios were prepared by methods similar to the one described in Preparation Example III. These catalysts are hereinafter referred to as Desulfurization Catalysts D and E, respectively.

(D) Cu:Fe:Al:O = 1:1.2:0:2.6–2.8
(E) Cu:Fe:Al:O = 1:1.2:2.0:5.6–5.8

EXAMPLE 1

Low Pressure Desulfurization

By using Desulfurization Catalyst A, perm kernel oil fatty acid methyl ester was desulfurized.

The desulfurization catalyst was extended into noodles (5 mm in the length and 2 mm in the diameter) with the use of bentonite. 270 cc of the molded product was packed in a reaction tube of 28 mm in the internal diameter. Then nitrogen gas containing 5 to 60% by volume of hydrogen was made to flow therethrough at 185° C. under atmospheric pressure at a gas flow rate of about 140 l/hr for 7.5 hours to thereby reduction-activating the desulfurization catalyst. Next, palm kernel oil fatty acid methyl ester of a sulfur content of 3.6 ppm and a hydrogen-containing gas were made to flow downward in parallel and thus the starting oil was desulfurized under a 100% hydrogen atmosphere while varying the conditions.

Tables 1-1 and 1-2 show the results of the analysis on the sulfur content of the obtained perm kernel oil fatty acid methyl ester. The sulfur content was measured with a Dohrmann type low concentration sulfur analyzer (System 701; product of Rosemount Analytical Inc.).

The recovery of the obtained palm kernel oil fatty acid methyl ester was substantially equal to 100%, which means that no palm kernel oil fatty acid methyl ester was lost in the desulfurization process.

TABLE 1-1

(Influence of LHSV and hydrogen flow rate at treatment temperature of 200° C. and treatment pressure of 1 kg/cm$^2$)

| LHSV (Hr$^{-1}$) | 2 | 2 | 2 | 4 |
|---|---|---|---|---|
| Hydrogen Flow Rate (Nl/Hr) | 700 | 1400 | 2300 | 2800 |
| Sulfur Content (ppm) | 1.46 | 0.17 | 0.13 | 0.48 |
| Acid Value (mgKOH/g) | 0.08 | 0.08 | 0.09 | 0.08 |

TABLE 1-2

(Influence of treating pressure and hydrogen flow rate at treating temperature of 200° C. and LHSV of 2 Hr$^{-1}$)

| Treating Pressure (kg/cm$^2$) | 2.5 | 2.5 | 10 | 10 |
|---|---|---|---|---|
| Hydrogen Flow Rate (Nl/Hr) | 700 | 2300 | 700 | 2300 |
| Sulfur Content (ppm) | 1.40 | 0.63 | 1.47 | 1.12 |
| Acid Value (mgKOH/g) | 0.08 | 0.09 | 0.01 | 0.02 |

EXAMPLE 2

Low Pressure Desulfurization

Palm kernel oil fatty acid methyl ester of a sulfur content of 3.6 ppm was desulfurized with Desulfurization Catalyst C in the same manner as described in Example 1. Tables 2 and 3 show the results obtained by treating under a 100% hydrogen atmosphere under various conditions.

The recovery of the obtained palm kernel oil fatty acid methyl ester was substantially equal to 100%, which means that no palm kernel oil fatty acid methyl ester was lost in the desulfurization process.

TABLE 2

(Influence of treating temperature, LHSV and hydrogen flow rate at treatment pressure of 1 kg/cm$^2$)

| LHSV (Hr$^{-1}$) | 2 | 2 | 2 | 4 |
|---|---|---|---|---|
| Hydrogen Flow Rate (Nl/Hr) | 700 | 1400 | 2300 | 2800 |
| Treating Temperature of 200° C. | | | | |
| Sulfur Content (ppm) | 1.89 | 0.11 | 0.01 | 0.24 |
| Acid Value (mgKOH/g) | 0.63 | 1.8 | 1.5 | 1.4 |
| Treating Temperature of 230° C. | | | | |
| Sulfur Content (ppm) | 0.62 | 0.01 | 0.01 | 0.06 |
| Acid Value (mgKOH/g) | 1.7 | 1.2 | 1.1 | 0.91 |

TABLE 3

(Influence of treating pressure and hydrogen flow rate at treating temperature of 230° C. and LHSV of 2 Hr$^{-1}$)

| Treating Pressure (kg/cm$^2$) | 5 | 5 | 10 | 10 |
|---|---|---|---|---|
| Hydrogen Flow Rate (Nl/Hr) | 700 | 2300 | 700 | 2300 |
| Sulfur Content (ppm) | 0.83 | 0.18 | 0.62 | 0.30 |
| Acid Value (mgKOH/g) | 0.37 | 0.70 | 0.52 | 0.22 |

EXAMPLE 3

Low Pressure Desulfurization

Palm kernel oil fatty acid methyl ester of a sulfur content of 3.6 ppm was desulfurized with Desulfurization Catalyst B in the same manner as described in Example 1. Table 4 shows the results obtained under the conditions as specified below.

Treating pressure: 1 kg/cm$^2$
Treating temperature: 200° C.
Gas and flow rate: 100% hydrogen gas, 230 Nl/hr The recovery of the obtained palm kernel oil fatty acid methyl ester was substantially equal to 100%, which means that no palm kernel oil fatty acid methyl ester was lost in the desulfurization process.

EXAMPLE 4

Low pressure Desulfurization

Desulfurization was effected in the same manner as described in Example 3 except that Desulfurization Catalyst D was used. Table 4 shows the result.

The recovery of the obtained palm kernel oil fatty acid methyl ester was substantially equal to 100%, which means that no palm kernel oil fatty acid methyl ester was lost in the desulfurization process.

EXAMPLE 5

Low pressure Desulfurization

Desulfurization was effected in the same manner as described in Example 3 except that Desulfurization Catalyst E was used. Table 4 shows the results.

The recovery of the obtained palm kernel oil fatty acid methyl ester was substantially equal to 100%, which means that no palm kernel oil fatty acid methyl ester was lost in the desulfurization process.

EXAMPLE 6

Low pressure Desulfurization

Desulfurization was effected in the same manner as described in Example 3 except that a marketed copper-chromium catalyst (Cu:Cr = 1:1) was used. Table 4 shows the results.

The recovery of the obtained palm kernel oil fatty acid methyl ester was substantially equal to 100%, which means that no palm kernel oil fatty acid methyl ester was lost in the desulfurization process.

TABLE 4

| | Example No. | | | |
|---|---|---|---|---|
| | 3 | 4 | 5 | 6 |
| Sulfur Content (ppm) | 0.11 | 0.18 | 0.13 | 0.41 |
| Acid Value (mgKOH/g) | 0.07 | 1.2 | 1.2 | 0.73 |

EXAMPLE 7

Low Pressure Desulfurization

Palm kernel oil fatty acid of a sulfur content of 4.0 ppm was desulfurized with Desulfurization Catalyst C in the same manner as described in Example 1. Table 5 shows the results obtained by treating under a 100% hydrogen atmosphere under various conditions.

The recovery of the obtained palm kernel oil fatty acid methyl ester was substantially equal to 100%, which means that no palm kernel oil fatty acid methyl ester was lost in the desulfurization process.

TABLE 5

| Treating Pressure (kg/cm$^2$) | 1 | 1 | 1 | 5 | 5 | 10 | 10 |
|---|---|---|---|---|---|---|---|
| LHSV (Hr$^{-1}$) | 2 | 2 | 4 | 2 | 2 | 2 | 2 |
| Hydrogen Flow Rate (Nl/Hr) | 1400 | 2300 | 2800 | 700 | 2300 | 700 | 2300 |
| Treating Temperature of 200° C. | | | | | | | |
| Sulfur Content (ppm) | 0.11 | 0.06 | 0.55 | 1.92 | 1.42 | 1.45 | 1.27 |
| Acid Value (mgKOH/g) | 1.6 | 1.6 | 1.3 | 0.41 | 0.85 | 0.61 | 0.43 |
| Treating Temperature of 230° C. | | | | | | | |
| Sulfur Content (ppm) | 0.06 | 0.04 | 0.23 | 1.13 | 0.33 | 1.01 | 0.62 |
| Acid Value (mgKOH/g) | 1.2 | 1.3 | 1.0 | 0.68 | 0.84 | 0.45 | 0.37 |

EXAMPLE 7

Low Pressure Desulfurization

Palm kernel oil fatty acid methyl ester of a sulfur content of 3.6 ppm was desulfurized with Desulfurization Catalyst C in the same manner as described in Example 1. Table 6 shows the results obtained by treating under a 100% nitrogen atmosphere, under a treating pressure of 1 kg/cm$^2$, at an LHSV of 2 Hr$^{-1}$ and at a nitrogen flow rate of 2300 Nl/hr.

The recovery of the obtained palm kernel oil fatty acid methyl ester was substantially equal to 100%, which means that no palm kernel oil fatty acid methyl ester was lost in the desulfurization process.

TABLE 6

| Treating Temperature (°C.) | 150 | 200 | 250 |
|---|---|---|---|
| Sulfur Content (ppm) | 2.13 | 0.42 | 0.36 |
| Acid Value (mgKOH/g) | 0.11 | 1.0 | 1.6 |

COMPARATIVE EXAMPLE 1

Distillation Desulfurization

For comparison, sulfur compounds contained in palm kernel oil fatty acid methyl ester were removed by distillation.

The same palm kernel oil fatty acid methyl ester as those used in the above Examples 1 to 6 was employed in this Comparative Example.

6 kg of the starting methyl ester was introduced into a 10 l evaporator and then distilled under reduced pressure (1-2 mmHg). When about 3 kg of the starting material was distilled, the starting methyl ester was further added and the distillation was continued. Thus 8.02 g of the methyl ester was purified in total. The sulfur content of the methyl ester thus distilled was determined to thereby examine the sulfur content against on the distillation ratio. Table 7 shows the obtained results.

TABLE 7

| Distillation Ratio of Starting Material (%) | 70.2 | 79.8 | 90.1 | 95.3 | 98.0 |
|---|---|---|---|---|---|
| Reduced Pressure Degree (mmHg) | 2.0 | 1.1 | 1.1 | 1.0 | 1.0 |
| Distillation Bottom Temperature (°C.) | 187 | 187 | 196 | 210 | 210 |
| Sulfur Content (ppm) | 0.17 | 0.25 | 0.33 | 0.49 | 0.72 |

At a distillation ratio of the starting material of 95%, the alkyl composition of the starting ester remaining as the distillation bottom comprised 80% or more of $C_{18}$ methyl esters. Therefore it is difficult to avoid the disadvantageously large loss of long chain methyl esters ($C_{16}$–$C_{18}$) by the distillation purification method.

EXAMPLE 9

Production of Alcohol

In order to examine the influences of the sulfur content in starting oils for reduction on the catalyst life of a catalyst for ester reduction, the oils obtained in the above Examples 1 to 6 and Comparative Example 1 were used as starting oils for reduction. Table 8 shows the starting oils for reduction used herein and Table 9 shows the results of the evaluation of the catalyst life of the catalyst for ester reduction effected by using these starting oils.

The catalyst for ester reduction used herein is a copper-zinc catalyst carried on titanium (CuO:ZnO:TiO$_2$=47.5%:2.5%:50.0%) disclosed in JP-A-1-305042 (the term "JP-A" as used herein means an "unexamined published Japanese patent application.") (corresponding to U.S. Pat. No. 4,918,248).

Evaluation of Activity Life of Catalyst for Ester Reduction

In a 0.5 l-volume autoclave equipped with a rotary stirrer, were charged 150 g of each of the starting oils and 3.75 g of the catalyst for ester reduction. The catalyst was activated in a hydrogen flow at a pressure of 10 kg/cm$^2$ and at a temperature of 200° C. for 2 hours. After elevating the temperature to 230° C. and the hydrogen pressure to 120 kg/cm$^2$, the reaction was started at a stirring rate of 800 rpm and at a hydrogen flow rate of 5 l/min. The reaction system was sampled appropriately in the course of the reaction and analyzed to obtain the conversion ratio of the starting ester whereby the catalyst activity was obtained. The reaction was adjusted as a first-order reaction with respect to the ester concentration and the rate constant per gram of the catalyst before activation was taken as a criterion of the catalyst activity.

After the completion of the reaction, the catalyst was separated from the alcohol thus produced by filtration and reused in the next reaction. This procedure was repeated 10 times under the same conditions and thus the rate constant was determined per reaction. A reduction of activity per reaction was calculated according to the following equation.

$$\text{Activity Reduction (\% per times)} = \frac{K_1 - K_{10}}{K_1} \times 100 \div \text{(time of use)}$$

where $K_1$ is a rate constant at the first time and $K_{10}$ is a rate constant at the tenth time.

In every experiment, the plots of rate constant against number of times of catalyst recovery revealed good linearity.

desulfurized in the present process is equal or longer than that using the distilled starting oil (distillation ratio=90.1%).

EXAMPLE 10

High Pressure Desulfurization

Palm kernel oil fatty acid methyl ester was desulfurized with Desulfurization Catalyst A.

The desulfurization catalyst was molded into noodles (5 mm in the length and 2 mm in the diameter) with the use of bentonite. 270 cc of the molded catalyst was fed into a high pressure reactor of 28 mm in the inner diameter. Then nitrogen gas containing 5 to 60% by volume of hydrogen was made to flow at 185° C. under atmospheric pressure at a rate of 140 l/hr for 7.5 hours. Thus the catalyst was pretreated. Then palm kernel oil fatty acid methyl ester of a sulfur content of 3.3 ppm and the hydrogen-containing gas were made to flow downward in parallel and thus sulfur compounds contained in the starting ester were removed under various conditions.

Tables 10 to 12 show the results of the analysis on the sulfur content of the palm kernel oil fatty acid methyl ester thus obtained.

The recovery of the obtained palm kernel oil fatty acid methyl ester was substantially equal to 100%, which means that no palm kernel oil fatty acid methyl ester was lost in the desulfurization process.

(1) Influence of Treating Temperature at Treating Pressure of 100 kg/cm$^2$

The influence of the treating temperature at a hydro-

TABLE 8

| Starting Oil | Desulfurization Process | Desulfurization Condition | Sulfur Content (ppm) | Acid Value (mgKOH/g) |
|---|---|---|---|---|
| a | Example 1 | 200° C., 1 kg/cm$^2$, LHSV = 2 Hr$^{-1}$ Hydrogen Flow Rate = 1400 Nl/Hr | 0.17 | 0.08 |
| b | Example 2 | 230° C., 10 kg/cm$^2$, LHSV = 2 Hr$^{-1}$ Hydrogen Flow Rate = 700 Nl/Hr | 0.62 | 0.52 |
| c | Example 2 | 230° C., 10 kg/cm$^2$, LHSV = 2 Hr$^{-1}$ Hydrogen Flow Rate = 2300 Nl/Hr | 0.30 | 0.22 |
| d | Example 3 | 200° C., 1 kg/cm$^2$, LHSV = 2 Hr$^{-1}$ Hydrogen Flow Rate = 2300 Nl/Hr | 0.11 | 0.07 |
| e | Example 4 | 200° C., 1 kg/cm$^2$, LHSV = 2 Hr$^{-1}$ Hydrogen Flow Rate = 2300 Nl/Hr | 0.18 | 1.2 |
| f | Example 5 | 200° C., 1 kg/cm$^2$, LHSV = 2 Hr$^{-1}$ Hydrogen Flow Rate = 2300 Nl/Hr | 0.13 | 1.2 |
| g | Example 6 | 200° C., 1 kg/cm$^2$, LHSV = 2 Hr$^{-1}$ Hydrogen Flow Rate = 2300 Nl/Hr | 0.41 | 0.73 |
| h | Comparative Example 1 | Distillation Ratio = 90.1% | 0.33 | 0.05 |

TABLE 9

| Starting Oil | Sulfur Content (ppm) | Activity Reduction (%/times) |
|---|---|---|
| a | 0.17 | 0.55 |
| b | 0.62 | 0.95 |
| c | 0.30 | 0.66 |
| d | 0.11 | 0.55 |
| e | 0.18 | 0.60 |
| f | 0.13 | 0.52 |
| g | 0.41 | 0.70 |
| h | 0.33 | 0.75 |

As the above results show, the activity reductions caused by using the starting oils whose sulfur content had been reduced to 0.6 ppm or less in the desulfurization process of the present invention (starting oils a, c, d, e, f and g) are smaller than that of the distilled methyl ester (staring oil h). Thus it is obvious that the activity life of the catalyst in a reaction using the starting oil gen pressure of 100 kg/cm$^2$, at an LHSV of the starting ester of 2 Hr$^{-1}$ and at a hydrogen/ester molar ratio* of 15 was examined.

*Hydrogen molar ratio = $\dfrac{\text{Molar Number of Feeding Hydrogen}}{\text{Molar Number of Ester Group in Starting Oil}}$ Table 10 shows the results.

TABLE 10

| | Temperature | |
|---|---|---|
| | 200° C. | 230° C. |
| Sulfur Content (ppm) | 0.58 | 0.09 |
| Saponification Value (mgKOH/g) | 49 | 23 |

TABLE 10-continued

|  | Temperature | |
| --- | --- | --- |
|  | 200° C. | 230° C. |
| Acid Value (mgKOH/g) | 0.01 | 0.01 |

(2) Influence of Treating Pressure

The influence of the treating pressure at an LHSV of the starting ester of 2.0 H$^{-1}$ and at a hydrogen/starting ester molar ratio of 15 was examined. Table 11 shows the results.

TABLE 11

|  | Pressure (kg/cm$^2$) | | | |
| --- | --- | --- | --- | --- |
|  | 30 | 50 | 100 | 230 |
| Sulfur Content (ppm) | 0.42 | 0.36 | 0.09 | 0.06 |
| Saponification Value (mgKOH/g) | 47 | 39 | 23 | 19 |
| Acid Value (mgKOH/g) | 0.01 | 0.01 | 0.01 | 0.01 |

(3) Influence of Hydrogen Molar Ratio

The influence of the hydrogen/ester molar ratio at a hydrogen pressure of 100 kg/cm$^2$, at an LHSV of the starting ester of 2 Hr$^{-1}$ and at a temperature 200° C. was examined. Table 12 shows the results.

TABLE 12

|  | H$_2$/Starting Material Molar Ratio | |
| --- | --- | --- |
|  | 15 | 50 |
| Sulfur Content (ppm) | 0.58 | 0.50 |
| Saponification Value (mgKOH/g) | 49 | 44 |
| Acid Value (mgKOH/g) | 0.01 | 0.01 |

EXAMPLE 11

High Pressure Desulfurization

Palm kernel oil fatty acid methyl ester was desulfurized by using Desulfurization Catalyst C.

The same conditions (molding, charging, reactor, pretreatment, starting ester) as those employed in Example 10 were used, except that Desulfurization Catalyst C was used. Thus sulfur compounds in the starting material were removed under various conditions.

(1) Influence of Treating Temperature at Treating Pressure of 100 kg/cm$^2$

The influence of the treating temperature at a hydrogen pressure of 100 kg/cm$^2$, at an LHSV of the starting ester of 2 Hr$^{-1}$ and at a hydrogen/ester molar ratio of 15 was examined. Table 13 shows the results.

TABLE 13

|  | Temperature | | |
| --- | --- | --- | --- |
|  | 200° C. | 230° C. | 250° C. |
| Sulfur Content (ppm) | 0.63 | 0.45 | 0.23 |
| Saponification Value (mgKOH/g) | 217 | 173 | 99 |
| Acid Value (mgKOH/g) | 0.29 | 0.26 | 0.11 |

(2) Influence of Treating Pressure

The influence of the treating pressure at an LHSV of the starting ester of 2 Hr$^{-1}$, at a hydrogen/starting ester molar ratio of 15 and at a treating temperature of 230° C. was examined. Table 14 shows the results.

TABLE 14

|  | Pressure (kg/cm$^2$) | | | |
| --- | --- | --- | --- | --- |
|  | 30 | 50 | 100 | 230 |
| Sulfur Content (ppm) | 0.45 | 0.10 | 0.04 | 0.02 |
| Saponification Value (mgKOH/g) | 173 | 130 | 76 | 36 |
| Acid Value (mgKOH/g) | 0.26 | 0.22 | 0.12 | 0.03 |

(3) Influence of Hydrogen Molar Ratio

The influence of the hydrogen/starting ester molar ratio at a hydrogen pressure of 30 kg/cm$^2$, at an LHSV of the starting ester of 2 Hr$^{-1}$ and at a temperature 200° C. was examined. Table 15 shows the results.

TABLE 15

|  | H$_2$/Starting Material Molar Ratio | | |
| --- | --- | --- | --- |
|  | 15 | 30 | 50 |
| Sulfur Content (ppm) | 0.45 | 0.33 | 0.21 |
| Saponification Value (mgKOH/g) | 173 | 164 | 153 |
| Acid Value (mgKOH/g) | 0.26 | 0.24 | 0.19 |

(4) Influence of LHSV

The influence of the LHSV at a hydrogen pressure of 100kg/cm$^2$, at a hydrogen/starting ester molar ratio of 15 and at a treating temperature of 230° C. was examined. Table 16 shows the results.

TABLE 16

|  | LHSV (Hr$^{-1}$) | | | |
| --- | --- | --- | --- | --- |
|  | 2 | 3 | 4 | 5 |
| Sulfur Content (ppm) | 0.04 | 0.11 | 0.18 | 0.31 |
| Saponification Value (mgKOH/g) | 76 | 109 | 135 | 158 |
| Acid Value (mgKOH/g) | 0.12 | 0.16 | 0.20 | 0.27 |

EXAMPLE 12

High Pressure Desulfurization

Palm kernel oil fatty acid methyl ester was desulfurized with the use of Desulfurization Catalyst B.

The desulfurization procedure employed in Example 10 was repeated except that Desulfurization Catalyst B was used.

Table 17 shows the results obtained at a treating temperature of 200° C., at an LHSV of the starting ester of 2 Hr$^{-1}$ and at a hydrogen/ester molar ratio of 15.

EXAMPLE 13 (i) AND (ii)

High Pressure Desulfurization

The procedure of Example 11 was repeated, except that the following Desulfurization Catalyst D (Example 13 (i)) or Desulfurization Catalyst E (Example 13 (ii)) was used, to thereby remove sulfur compounds contained in the starting ester.

Table 17 shows the results obtained at a treating temperature of 200° C., at a treating pressure of 230 kg/cm$^2$, at an LHSV of the starting ester of 2 Hr$^{-1}$ and at a hydrogen/ester ratio of 15.

EXAMPLE 14

High Pressure Desulfurization

The procedure of Example 13 was repeated, except that a marketed copper-chromium catalyst (Cu:Cr=1:1) was used, to thereby remove sulfur compounds contained in the starting ester. Table 17 shows the results obtained at a treating temperature of 200° C., at a treating pressure of 230 kg/cm², at an LHSV of the starting ester of 2 Hr⁻¹ and at a hydrogen/ester ratio of 15.

TABLE 17

| | Example No | | | |
|---|---|---|---|---|
| | 12 | 13 (i) | 13 (ii) | 14 |
| Catalyst | B | D | E | Cu—Cr |
| Sulfur Content (ppm) | 0.13 | 0.11 | 0.24 | 0.54 |
| Saponification Value (mgKOH/g) | 85 | 88 | 127 | 151 |
| Acid Value (mgKOH/g) | 0.01 | 0.11 | 0.15 | 0.22 |

EXAMPLE 15

High Pressure Desulfurization

The procedure of Example 11 was repeated except that coconut oil fatty acid methyl ester of a sulfur content of 3.3 ppm was used as the starting material. Thus sulfur compounds were removed. Table 18 shows the results of the examination on the influence of treating temperature at a hydrogen pressure of 50 kg/cm², at an LHSV of the starting ester of 2 and at a hydrogen/ester molar ratio of 15.

TABLE 18

| | Temperature | | |
|---|---|---|---|
| | 200° C. | 230° C. | 250° C. |
| Sulfur Content (ppm) | 0.57 | 0.24 | 0.10 |
| Saponification Value (mgKOH/g) | 173 | 116 | 78 |
| Acid Value (mgKOH/g) | 0.29 | 0.25 | 0.21 |

EXAMPLE 16

High Pressure Desulfurization

The procedure of Example 11 was repeated except that deacidified and purified palm kernel oil of a sulfur content of 4.0 ppm was used as the starting material. Thus sulfur compounds were removed. Table 19 shows the results of the examination on the influence of treating temperature at a hydrogen pressure of 100 kg/cm², at an LHSV of the starting ester of 2 Hr⁻¹ and at a hydrogen/ester molar ratio of 15.

TABLE 19

| | Temperature | | | |
|---|---|---|---|---|
| | 180° C. | 200° C. | 230° C. | 250° C. |
| Sulfur Content (ppm) | 0.62 | 0.45 | 0.17 | 0.11 |
| Saponification Value (mgKOH/g) | 213 | 168 | 127 | 103 |
| Acid Value (mgKOH/g) | 0.32 | 0.26 | 0.23 | 0.18 |

EXAMPLE 17

High Pressure Desulfurization

To a 0.5 l-volume autoclave equipped with a rotary stirrer, were charged 15 g of a reduction activated catalyst contained in a basket reactor and 200 g of the starting oil. After elevating the temperature to 250° C. and the pressure to the desulfurization was effected at a stirring rate of 800 rpm and at a hydrogen flow rate of 5 l/min for 3 hours. As the catalyst, Desulfurization Catalyst A or C was employed, while palm kernel oil fatty acid methyl ester used in Example 10 was employed as the starting oil. Table 20 shows the results thus obtained.

TABLE 20

| | Desulfurization Catalyst A | Desulfurization Catalyst C |
|---|---|---|
| Sulfur Content (ppm) | 0.37 | 0.16 |
| Saponification Value (mgKOH/g) | 78 | 90 |
| Acid Value (mgKOH/g) | 0.04 | 0.09 |

EXAMPLE 18

High Pressure Desulfurization

To a 0.5 l-volume autoclave equipped with a rotary stirrer, were charged 3.75 g of a powdery catalyst and 150 g of dodecyl alcohol. After elevating the temperature to 200° C., the catalyst was activated at a hydrogen pressure of 10 kg/cm², at a stirring rate of 800 rpm and at a hydrogen flow rate of from 8 to 10 l/min for 2 hours. Then the powdery catalyst was separated by means of centrifugation and the total amount of the catalyst thus separated and 150 g of a starting oil (palm kernel oil fatty acid methyl ester) were fed into the aforesaid autoclave again. After elevating the temperature to 250° C., the starting oil was desulfurized at a hydrogen pressure of 230 kg/cm², at a stirring rate of 800 rpm and at a hydrogen flow rate of 5 l/min. After 2 hours, the reaction mixture was sampled and the obtained sample was filtered to thereby remove the catalyst. The desulfurized oil thus obtained was analyzed. As the catalyst, Desulfurization Catalyst A or C was used.

Table 21 shows the results.

TABLE 21

| | Desulfurization Catalyst A | Desulfurization Catalyst C |
|---|---|---|
| Sulfur Content (ppm) | 0.59 | 0.33 |
| Saponification Value (mgKOH/g) | 24 | 42 |
| Acid Value (mgKOH/g) | 0.02 | 0.03 |

The purification recovery of each of the starting esters treated in the above Examples 10 to 18 was substantially equal to 100%, which means that no starting material was lost in purification process.

EXAMPLE 19

Production of Alcohol

In order to examine the influences of the sulfur content in starting oils for reduction on the catalyst life of a catalyst for ester reduction, the treated oils obtained in Examples 10 to 18 and Comparative Example 1 were used as starting oils for reduction. Table 22 shows the starting oils for reduction used herein and Table 23 shows the results of the evaluation of the catalyst life of the catalyst for ester reduction effected by using these starting oils.

The catalyst for ester reduction used herein is a copper-zinc catalyst carried on titanium (CuO:ZnO:TiO₂ = 47.5%:2.5%:50.0%) disclosed in JP-A-1-305042

Evaluation of Activity Life of Catalyst for Ester Reduction

The evaluation was effected by the same method as described in Example 9.

TABLE 22

| Starting Oil | Desulfurization Process | Desulfurization Condition | Sulfur Content (ppm) |
|---|---|---|---|
| i | Example 10 | 230° C., 50 kg/cm², LHSV = 2 Hr⁻¹ H₂/Starting Material Molar Ratio = 15 | 0.36 |
| j | Example 11 | 200° C., 100 kg/cm², LHSV = 2 Hr⁻¹ H₂/Starting Material Molar Ratio = 15 | 0.63 |
| k | Example 11 | 230° C., 100 kg/cm², LHSV = 2 Hr⁻¹ H₂/Starting Oil Material Ratio = 15 | 0.45 |
| l | Example 12 | 200° C., 230 kg/cm², LHSV = 2 Hr⁻¹ H₂/Starting Material Molar Ratio = 15 | 0.13 |
| m | Example 13 (ii) | 200° C., 230 kg/cm², LHSV = 2 Hr⁻¹ H₂/Starting Material Molar Ratio = 15 | 0.24 |
| n | Example 15 | 250° C., 50 kg/cm², LHSV = 2 Hr⁻¹ H₂/Starting Material Molar Ratio = 15 | 0.33 |
| h | Comparative Example 1 | Distillation Ratio = 90.1% | 0.33 |
| p | — | Untreated Palm Kernel Oil Fatty Acid Methyl Ester | 3.3 |

TABLE 23

| Starting Oil | Sulfur Content (ppm) | Activity Reduction (%/time) |
|---|---|---|
| i | 0.36 | 0.70 |
| j | 0.63 | 1.03 |
| k | 0.45 | 0.72 |
| l | 0.13 | 0.55 |
| m | 0.24 | 0.59 |
| n | 0.33 | 0.67 |
| h | 0.33 | 0.75 |
| p | 3.3 | 6.75 |

As the above results show, the activity reductions obtained by using the starting oils whose sulfur content had been reduced to 0.6 ppm or less by the desulfurization process of the present invention (starting materials i, j, k, l, m and n) are smaller than that of the distilled methyl ester (staring oil h). Thus it is obvious that the activity life of the catalyst in a reaction using the starting oil desulfurized in the present process is equal or longer than that of the catalyst in a reaction using the distilled starting oil (distillation ratio =90.1%).

EXAMPLE 20

Production of Alcohol

The time required for the formation of an alcohol was examined.

The time required for the formation of an alcohol through ester reduction was examined by using the starting oils for reduction obtained in the above Examples. The starting oils for reduction used herein were k, m, h and p, where h and p are for comparison, listed in Table 22 each having the saponification value as specified in Table 24.

TABLE 24

|  | Starting Oil | | | |
|---|---|---|---|---|
|  | K | m | h | p |
| Saponification Value (mgKOH/g) | 173 | 127 | 252.2 | 249.9 |

The reaction was effected by using the same catalyst and under the same conditions each as those employed in Example 10. The time required for achieving the saponification value (SV) to 10 mgKOH/g was referred to as the time for the formation of the alcohol. Table 25 shows the results thus obtained.

TABLE 25

|  | Starting Oil | | | |
|---|---|---|---|---|
|  | K | m | h | p |
| Reaction Time (min.) (Saponification Value (mgKOH/g) = 10) | 72 | 63 | 98 | 106 |

The above results show that the reaction time for the formation of the alcohol can be shortened by using the starting oils for reduction obtained by the treatments described in the above Examples, as compared with a case where purification is effected by distillation or the untreated starting material is employed.

According to the present invention, fats and oils or fatty acid esters of reduced sulfur content can be very efficiently produced.

According to the process for producing alcohols of the present invention, further, the activity life of a catalyst for ester reduction to be used in the production of alcohols from fats and oils or fatty acid esters can be extended.

According to the present invention, furthermore, highly pure alcohols of good qualities can be efficiently and effectively produced by efficiently reducing the sulfur content of fats and oils or fatty acid ester and then hydrogenating the fats and oils or fatty acid esters thus obtained in the presence of a catalyst for ester reduction.

While the invention has been described in detail and with reference to specific examples thereof, it will be apparent to one skilled in the art that various changes and modifications can be made therein without departing from the spirit and scope thereof.

What is claimed is:

1. A process for producing desulfurized fats and oils or fatty acid esters which comprises treating fats and oils or fatty acid esters under a hydrogen or a mixture of hydrogen and an inert gas atmosphere at a temperature of from 100° to 350° C. in the presence of a catalyst represented by the following formula (I):

$$Cu \cdot X_x \cdot Y_y \cdot O_z$$

wherein X represents an element selected from Fe, Zn and Cr;

Y represents an element selected from Al, Si and Ti;

x and y each represent an atomic ratio determined by referring to Cu as 1, provided that x is a value of from 0.02 to 2.4 and y is a value of from 0 to 2.0; and z is an atomic ratio of oxygen satisfying the valence requirements of the elements represented by X and Y.

2. The process of claim 1, wherein the pressure of the hydrogen or the mixture of hydrogen and the inert gas is from 0.1 to 20 kg/cm$^2$ in absolute pressure.

3. The process of claim 1, wherein the pressure of the hydrogen or the mixture of hydrogen and the inert gas is controlled from more than 20 kg/cm$^2$ to 500 kg/cm$^2$ in absolute pressure.

4. The process of claim 1, wherein said process is carried out in a continuous reaction system.

5. The process of claim 4, wherein said continuous reaction system is a fixed bed continuous reaction system.

6. The process of claim 1, wherein said process is carried out to yield a sulfur content of said fats and oils or fatty acid esters of 0.6 ppm or less.

7. The process of claim 6, wherein said process is carried out to yield a sulfur content of said fats and oils or fatty acid esters of less than 0.3 ppm.

8. The process of claim 1, wherein said process is carried out to yield an acid value of said fats or oils or fatty acid esters of 2 mgKOH/g or less.

9. The process of claim 3, wherein said process is carried out to yield a saponification value of said fats and oils or fatty acid esters of 180 mgKOH/g or less.

* * * * *